United States Patent [19]
Smerbeck et al.

[11] Patent Number: 5,958,397
[45] Date of Patent: Sep. 28, 1999

[54] METHOD AND COMPOSITION FOR PROTECTING AGAINST JELLYFISH STINGS

[75] Inventors: Richard V. Smerbeck, Pittsford, N.Y.; James R. Johnson, Germantown, Tenn.; Joseph W. Burnett, Baltimore; Jennifer E. Purcell, Easton, both of Md.

[73] Assignees: Schering-Plough HealthCare Products, Inc., Memphis, Tenn.; University of Maryland, Baltimore, Baltimore, Md.

[21] Appl. No.: 08/897,268

[22] Filed: Jul. 21, 1997

Related U.S. Application Data

[60] Provisional application No. 60/022,030, Jul. 22, 1996.
[51] Int. Cl.$^6$ .............................. A61K 31/74; A61K 7/42; A61K 7/00; A61K 31/14
[52] U.S. Cl. ...................... 424/78.03; 424/59; 424/78.02; 424/401; 514/642; 514/829; 514/862
[58] Field of Search .......................... 424/401, 59, 78.02, 424/78.03; 514/642, 829, 862

[56] References Cited

U.S. PATENT DOCUMENTS

| | | | |
|---|---|---|---|
| 2,372,159 | 3/1945 | Manchey | 167/91 |
| 3,769,242 | 10/1973 | Kelly et al. | 252/542 |
| 4,438,095 | 3/1984 | Grollier et al. | 424/70 |
| 4,781,918 | 11/1988 | Hofinger et al. | 424/70 |
| 4,871,530 | 10/1989 | Grollier et al. | 424/47 |
| 5,011,583 | 4/1991 | Olney | 514/454 |
| 5,013,763 | 5/1991 | Tubesing et al. | 514/772 |
| 5,439,682 | 8/1995 | Wivell et al. | 724/401 |

FOREIGN PATENT DOCUMENTS

| | | |
|---|---|---|
| 471453 | 4/1976 | Australia . |
| 544091 | 5/1985 | Australia . |
| 0 610 926 A1 | 8/1994 | European Pat. Off. . |
| 2 110 534 | 6/1983 | United Kingdom ........... A61K 33/06 |

OTHER PUBLICATIONS

Burnett et al., "Studies on Sea Nettle Stings", Arch Derm, V. 98, pp.587–589, 1968.

Heeger et al., "Protection of human skin against jellyfish (*Cyanea capillata*) stings", Marine Biology, V. 113, pp. 669–678, 1992.

Merquat 550, Specialty Chemicals, Calgon Corporation, Bulletin and MSDS.

Abstract of EP 0 475 479 B.

Abstract of RU 2021721 C.

Abstract of JP 7216856 A.

Abstract of JP 7292646 A.

Abstract of FR 2439845 A.

Abstract of SU 917829 A.

Abstract of DE2541126 A.

J. W. Burnett et al., "A Physical and Chemical Study of Sea Nettle Nematocysts and Their Toxin," *Journal of Investigative Dermatology*, vol. 61, pp. 330–336, 1968.

R. Mansueti, "The Sea Nettle, Chesapeake Bay's Troublesome Summer Jellyfish," *Maryland Tidewater News*, vol. 12, No. 3, Supp. 7, Revised Ed. Sep. 1962, 2 pp.

R. Lubbock, "Chemical Recognition and Nematocyte Excitation in a Sea Anemone," *Journal of Experimental Biology*, vol. 83, pp. 283–292, 1979.

A. Salleo, "Gadolinium is a Powerful Blocker of the Activation of Nematocytes of *Pelagia Noctiluca*," *Journal of Experimental Biology*, vol. 187, pp. 201–206, 1994.

"SALCARE SC96 for Hair Care," publication of Allied Colloids, Suffolk, Virginia U.S.A., 3 pp., publication date unknown.

*Primary Examiner*—Shelley A. Dodson
*Assistant Examiner*—Marina Lamm
*Attorney, Agent, or Firm*—Joseph T. Majka; Robert A. Franks

[57] ABSTRACT

The present invention is directed towards a method, a composition and an article of manufacture for protecting the skin from jellyfish stings. The method comprises topically contacting the skin with a composition containing polymeric quaternary ammonium salt in amounts sufficient to protect against the rupture of jellyfish nematocysts. The composition can be in the form of an emulsion, liquid dispersion, solution, skin cream, face cream, lotion or ointment.

19 Claims, No Drawings

METHOD AND COMPOSITION FOR PROTECTING AGAINST JELLYFISH STINGS

CROSS-REFERENCE TO RELATED APPLICATION

This application claims the benefit under 35 U.S.C. § 119(e) of provisional application Ser. No. 60/022,030 filed Jul. 22, 1996.

BACKGROUND

Jellyfish, including sea nettles (*Chrysaora quinquecirrha*) and Portuguese man-of-war (*Physalia physalis*), are aquatic organisms capable of stinging human tissues and cause local pain. Jellyfish fire toxin-coated harpoons from millions of intra-cellular organelles (nematocysts) into the nerve-rich human dermis, producing instant local pain. The pain and associated rash and swelling can persist for hours to weeks, depending on the species of jellyfish and the person's sensitivity. Many of these stings can cause severe injury and there are also cases reported of deaths.

The jellyfish stinging problem is prominent in the tropical and subtropical regions. In the United States, the stinging problem is particularly troublesome along the shores of the Eastern United States and Gulf Coast. Two species are responsible for most of the reported stings, the sea nettle, which is extremely abundant in the Chesapeake Bay, and the Portuguese man-of-war, which is blown by winds into beach areas, especially in Florida and Texas. It is estimated that approximately one to two million jellyfish sting cases occur annually along these shores. One approach to the stinging problem includes thick mechanical barriers such as clothing. The most common prevention treatment has been to coat the skin with petrolatum or other greasy or oily materials. Australia Patent Specification 44,159/72 (1974) teaches the use of petrolatum and silicone oils to protect against jellyfish stings. Other treatments include those taught in UK Patent Application 2110534 A (1983); EP 610,926 A1 (1994); J. Burnett et al, "A Physical and Chemical Study of Sea Nettle Nematocysts and their toxin", Journal of Investigative Dermatology, Vol. 61, No. 5, pp. 330–336 (1968); A. Salleo, "Gadolinium is a Powerful Blocker of the Activation of Nematocytes of *Pelagia noctiluca*", J. Exp. Biol, pp.1–6, (1994); and T. Heeger et. al., "Protection of human skin against jellyfish (*Cyanea capillata*) stings, Marine Biology 113, pp. 669–678 (1992).

Accordingly, a different approach was sought to protect against jellyfish stings.

SUMMARY OF THE INVENTION

We have discovered that the rupture of jellyfish nematocysts could be reduced with a topical composition containing a polymeric quaternary ammonium emulsifier, preferably a polymeric quaternary ammonium salt.

In one embodiment, the present invention is directed towards a method for protecting the skin from jellyfish stings, comprising topically contacting the skin with a composition containing polymeric quaternary ammonium salt in amounts sufficient to protect against the rupture of jellyfish nematocysts. The amount of polymeric quaternary ammonium salt in the composition can range from about 0.25% to about 20 weight %, more preferably from about 0.5% to about 5%. Preferably, the polymeric quaternary ammonium salt is Polyquaternium-7, Polyquaternium-10, Polyquaternium-37 or mixtures thereof. Preferably, the composition contains one or more sunscreen actives to protect against the actinic radiation of the sun.

The present invention is also directed toward a composition for reducing the rupture or stings of nematocysts from jellyfish, wherein said composition comprises a protective agent which is a polymeric quaternary ammonium salt employed in amounts effective to protect against the rupture or stings of jellyfish nematocysts. The composition can be in the form of an emulsion, liquid dispersion, solution, skin cream, face cream, lotion or ointment.

The present invention is also directed toward an article of manufacture comprising packaging material and a composition comprising a protective agent which is a polymeric quaternary ammonium salt contained within said packaging material, wherein said protective agent is effective in protecting against the rupture or stings of jellyfish nematocysts and wherein said packaging material comprises a label which indicates that said protective agent can be used to protect against jellyfish stings.

It is surprising and unexpected that a compositions of the invention comprising one or more polymeric quaternary ammonium salts can offer excellent protection against attacks by Cnidaria, the discharge of the stinging capsules, and the penetration of the stinging threads or the stinging poison into the skin. The compositions of the present invention can be applied to the skin in amounts normally used for topical preparations before the possibility of contact with these animals.

The present invention has the advantage of providing a method, a composition and an article of manufacture for protecting the skin from the stinging or toxic effects of jellyfish contact.

A second advantage of the present invention is that it provides a composition for protecting the skin from jellyfish contact that is compatible with other active materials such as sunscreen actives and may be formulated into numerous formulations, e.g. sunscreen emulsions, skin creams, face creams, lotions or ointments.

A third advantage of the present invention is that unlike other known methods for protecting the skin from jellyfish stings that employ mechanical barriers such as clothing, thick greases and cages, the present invention provides a portable, convenient and/or relatively inexpensive means which is more cosmetically acceptable to the public, including bathers, swimmers and fishermen.

DETAILED DESCRIPTION OF THE INVENTION

For purposes of the present patent specification, the terms "reducing", "preventing," "protecting or protecting against" as related to the rupture or stings of nematocysts from jellyfish are substantially synonymous and can be used interchangeably.

The compositions of the present invention containing one or more polymeric quaternary ammonium salts can be formulated into emulsions, liquid dispersions, solutions, skin creams, face creams, lotions or ointments. Such compositions may contain emulsifiers, water, emollients, dry-feel agents, waterproofing agents, preservatives, antioxidants, anti-foaming agents and fragrances as well as any other class of materials whose presence may be cosmetically, or otherwise desirable.

Emulsions/Emulsifiers

An emulsion is a mixture of two immiscible liquids, i.e. liquids that are not mutually soluble, but are mechanically agitated and shaken so thoroughly together that one liquid forms drops in the other one, giving the mixture the appearance of a homogeneous liquid. If the emulsifier is added to the two immiscible liquids, one of them becomes continuous and the other one remains in droplet form. As used herein in reference to the water-in-oil emulsifiers, the term "HLB value" means the hydrophilic-lipophilic balance. The HLB value has been used by those skilled in the emulsion art for selecting emulsifiers useful for preparing water-in-oil emulsions. See U.S. Pat. No. 4,177,259 and references cited therein.

An oil-in-water (o/w) emulsion is a mixture where oil droplets (the discontinuous phase) are dispersed in water (a continuous aqueous phase). A water-in-oil (w/o) is a mixture where water droplets (the discontinuous phase) are dispersed in oil (a continuous oil phase). Preferably the composition of the present invention is an oil-in-water emulsion where the oil-soluble actives are dispersed in the oil phase, prior to mixture with the water phase. The type of emulsion, oil-in-water (o/w) or water-in-oil (w/o) is determined by the volume ratio of the two liquids provided the ratio is sufficiently high. For example, with 5% water and 95% oil (an o/w phase ratio of 19), the emulsion likely will become w/o. For moderate ratios (<3), the type of emulsion is decided by several factors, such as order of addition or type of emulsifier. One liquid slowly added to a second liquid with agitation usually results in the second liquid being the continuous phase. Another factor is preferred solubility of the emulsifier, the phase in which the emulsifier is soluble most probably is continuous.

More complex emulsions such as double emulsions are formed where an emulsion is dispersed in an continuous phase. For example, in an oil in-water-in oil (o/w/o) emulsion, the water in a continuous water phase containing dispersed oil droplets, are themselves dispersed in a continuous oil phase. Similarly, in a water-in oil-in water emulsion, the oil in a continuous phase containing dispersed water droplets, are themselves dispersed in a continuous water phase. These more complex emulsions find use as a system for slow delivery, extraction, etc.

An emulsifier (a stabilizing compound) is an agent used to assist in the production of an emulsion. Typically, emulsifiers are molecules with non-polar and polar parts that are able to reside at the interface of the two immiscible liquids.

The term "polymeric quaternary ammonium salt" refers to a cationic charged macromolecule formed by the covalent bonding of five or more identical combining units called monomers, wherein each monomer contains at least one nitrogen atom joined to four organic groups as well as to an anionic radical. The polymeric quaternary ammonium salt can also refer to a cationic charged copolymer of two or more different monomers wherein at least one of the monomers contains at least one nitrogen atom joined to four organic groups as well as to an anionic radical.

Exemplary polymeric quaternary ammonium salts include, but are not limited to the following. Information obtained from the International Cosmetic Ingredient Dictionary, pages 570–574.

General Monomer/Polymer Description

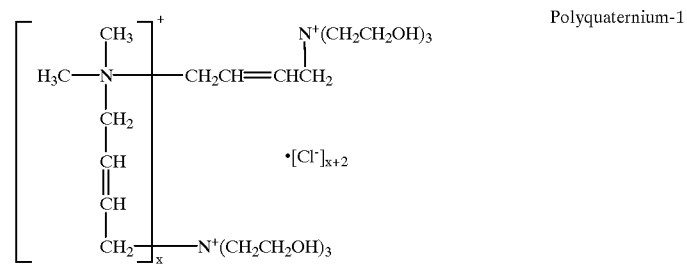

Polyquaternium-1

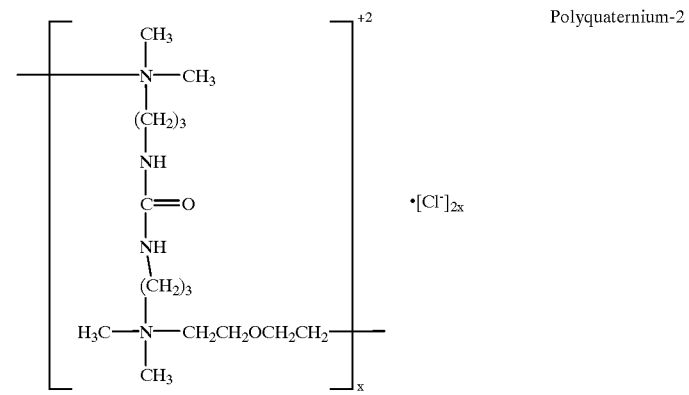

Polyquaternium-2

The copolymer of hydroxyethylcellulose and diallyldimethyl ammonium chloriode.
Technical Name: Diallyldinonium Chloride/Hydroxyethylcellulose Copolymer Polyquaternium-4

The copolymer of acrylamide and beta-methacryloxyethyl trimethyl ammonium

Polyquaternium-5

| General Monomer/Polymer Description | |
|---|---|
| methosulfate.<br>Technical name: Ethanaminium, N,N,N-Trimethyl-2-[(2-Methyl-1-Oxo-2-Propenyl)Oxy]-, Methyl Sulfate, Polymer with 2-Propenamide | |
| $(C_8H_{16}N\bullet Cl)_x$ | Polyquaternium-6 |
| The polymer of dimethyl diallyl ammonium chloride.<br>Technical Name: N,N-Dimethyl-N-2-Propenyl-2-Propen-1-aminium Chloride, Homopolymer | |
| $(C_8H_{16}N\bullet C_3H_5NO\bullet Cl)$ | Polyquaternium-7 |
| The polymeric quaternary ammonium salt consisting of acrylamide and dimethyl diallyl ammnium chloroide monomers.<br>Technical Name: N,N-Dimethyl-N-2-Propenyl-2-1-aminium Chloride, Polymer with 2-Propenamide | |
| The polymeric quaternary ammonium salt of methyl and stearyl dimethylaminoethyl methacrylate quaternized with dimethyl sulfate.<br>Technical Name: Methyl and Stearyl Dimethylamiunoethyl Methacrylate Quaternized with Dimethyl Sulfate | Polyquaternium-8 |
| The polymeric quaternary ammonium salt of polydimethylaminoethyl methacrylate quaternized with methyl bromide.<br>Technical Name: Polydimethylaminoethyl Methacryklate Quaternized with Methyl Bromide | Polyquaternium-9 |
| The polymeric quaternary ammonium salt of hydroxyethyl cellulose reacted with a trimethyl ammonium substituted epoxide.<br>Technical Name: Cellulose, 2-Hydroxyethyl-2-Hydroxy-3-(Trimethylammonio)Propyl Ether, Chloride | Polyquaternium-10 |
| $(C_8H_{15}NO_2\bullet C_6H_9NO)_x\bullet xC_4H_{10}O_4S$ | Polyquaternium-11 |
| The quaternary ammonium polymer formed by the reaction of diethyl sulfate and a copolymer of | vinyl pyrrolidone and dimethyl |
| aminoethylmethacrylate.<br>Technical Name: 2-Propenol Acid, 2-Methyl-2-(Dimethylamino)Ethyl Ester, Polymer and 1-Ethenyl-2-Pyrrolidinone, Compound with Diethyl Sulfate | |
| The polymeric quaternary ammonium salt prepared by the reaction of ethyl methacrylate/abietyl methacrylate/diethylaminoethyl methacrylate copolymer with dimethyl sulfate. | Polyquaternium-12 |
| The polymeric quaternary ammonium salt prepared by the reaction of ethyl methacrylate/oleyl methacrylate/diethylaminoethyl methacrylate copolymer with dimethyl sulfate | Polyquaternium-13 |

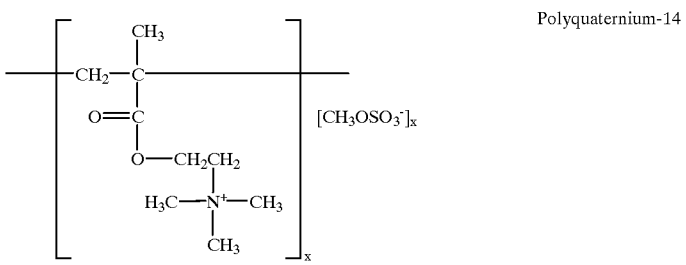

Polyquaternium-14

Technical Name: Ethanaminium, N,N,N-Trimethyl-2-[(2-Methyl-1-Oxo-2-Propenyl)Oxy], Methyl Sulfate, Homopolymer

| The copolymer of acrylamide and betamethacrylyl-oxyethyl trimethyl ammonium chloride. | Polyquaternium-15 |
|---|---|
| The polymeric quaternary ammonium salt formed from methyl-vinylimidazolium chloride and vinylpyrrolidone. | Polyquaternium-16 |

-continued

| General Monomer/Polymer Description | |
|---|---|
| 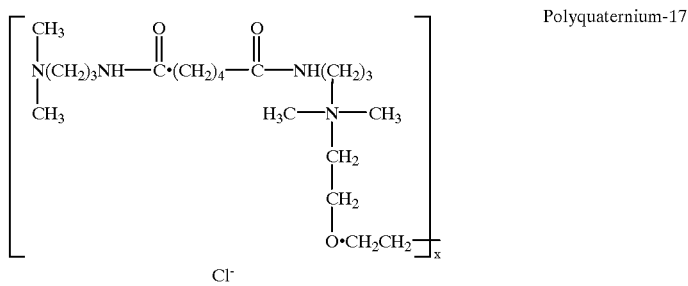<br>Cl<sup>-</sup><br>Polymeric quaternary salt prepared by the reaction of adipic acid and dimethylaminopropylamine with dichloroethyl ether. | Polyquaternium-17 |
| 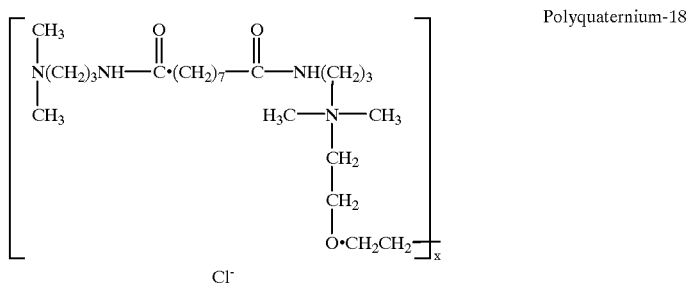<br>Cl<sup>-</sup><br>The polymeric quaternary salt prepared by the reaction of azelaic acid and dimethylaminopropylamine reacted with dichloroethyl ether. | Polyquaternium-18 |
| The polymeric quaternary ammonium salt prepared by the reaction of polyvinyl alcohol with 2,3-epoxy-propylamine. | Polyquaternium-19 |
| The polymeric quaternary ammonium salt prepared by the reaction of polyvinyl octadecyl with 2,3-epoxy-propylamine. | Polyquaternium-20 |
| 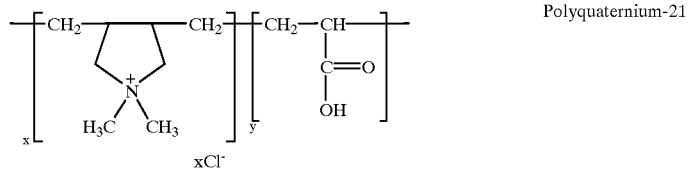<br>xCl<sup>-</sup><br>The copolymer of dimethyldiallyl ammonium chloride and acrylic acid. | Polyquaternium-21 |
| The polymeric quaternary ammonium salt of hydroxyethyl cellulose reacted with a lauryl dimethyl ammonium substituted epoxide. | Polyquaternium-22 |
| The block copolymer formed by the reaction of Polyquaternium-2 with Polyquaternium-17 | Polyquaternium-27 |
| 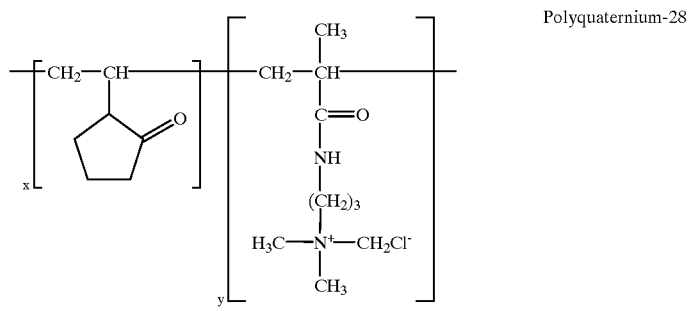<br>Technical Name:<br>Vinylpyrrolidone/Methacrylamidopropyltri-methylammonium Chloride Copolymer | Polyquaternium-28 |
| Chitosan (q.v.) that has been reacted with | Polyquaternium-29 |

| General Monomer/Polymer Description | |
|---|---|
| propylene oxide and quaternized with epichlorohydrin. | |
| 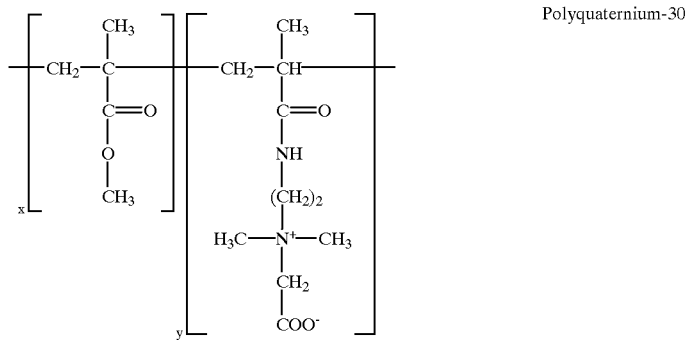 | Polyquaternium-30 |
| Technical Name: 2-Propeneitrile, Homopolymer, Hydrolyzed, Block Reaction Products with N,N-Dimethyl-1,3-Propanediamine, Di-Et Sulfate-Quaternized | |
| 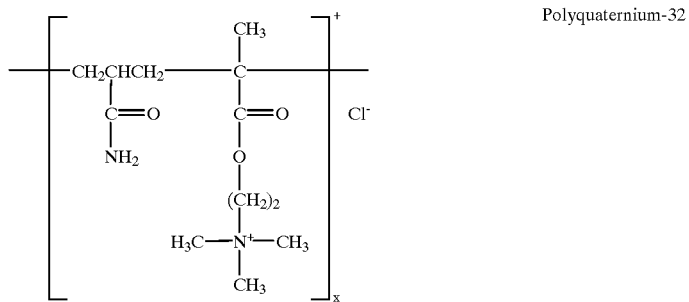 | Polyquaternium-32 |
| Technical Name: Ethanaminium, N,N,N-Trimethyl-2-[(2-Methyl-1-Oxo-2-Propenyl)Oxyl], Chlorode, Polymer with 2-Propenamide | |
| 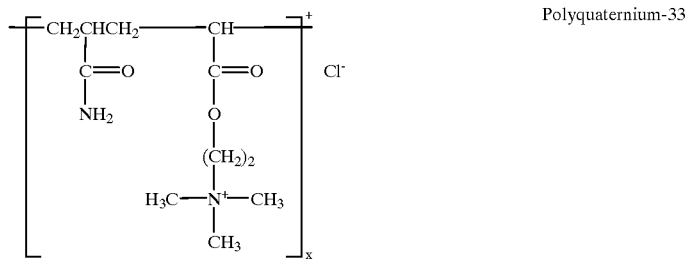 | Polyquaternium-33 |
| Technical Name: Ethanaminium, N,N,N-Trimethyl-2[1-Oxo-2-Propenyl)Oxyl]-, Chloride Poly,er with 2-Propenamide | |
| 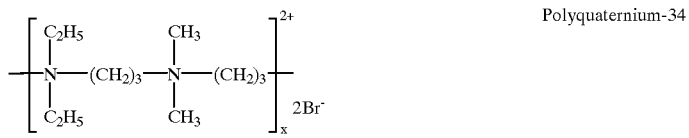 | Polyquaternium-34 |

General Monomer/Polymer Description

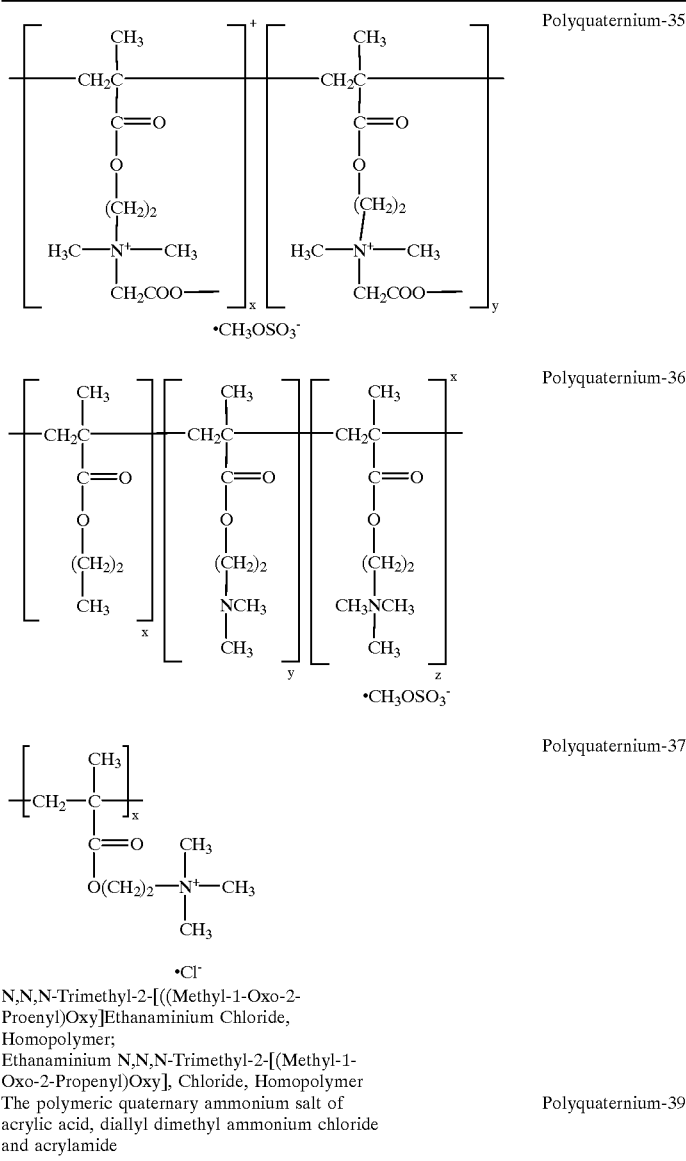

Polyquaternium-35

Polyquaternium-36

Polyquaternium-37

N,N,N-Trimethyl-2-[((Methyl-1-Oxo-2-Proenyl)Oxy]Ethanaminium Chloride, Homopolymer;
Ethanaminium N,N,N-Trimethyl-2-[(Methyl-1-Oxo-2-Propenyl)Oxy], Chloride, Homopolymer
The polymeric quaternary ammonium salt of acrylic acid, diallyl dimethyl ammonium chloride and acrylamide Polyquaternium-39 wherein x, y and z can each independently represents an integer from 0 to several hundred or several thousand or several hundred thousand or more and wherein $x+y+z \geq 5$. The above polymeric quaternary ammonium salts can be employed alone or in mixtures of two or more other quaternary ammonium salts. Alternatively or in addition, the above quaternary ammonium salts can be mixed or combined with other types of emulsifiers.

Preferably the polymeric quaternary ammonium salt is Polyquaternium-7, Polyquaternium-10, Polyquaternium-37 or mixtures thereof, preferably Polyquaternium-37. A commercially available solution containing Polyquaternium-7 is known as Merquat®550, trademark of the Calgon Corporation, Pittsburgh, Pa. Merquat®550 is an 8% aqueous solution of a highly charged cationic copolymer of dimethy-idiallyammonium chloride and acrylamide. A commercially available solution containing Polyquaternium-10 is known as UCARE Polymer JR-30M, trade name of Amerchol Corporation. A commercially available solution containing Polyquaternium-37 is known as Salcare SC96, trade name of Allied Colloids, Suffolk, Va. Salcare 96 contains the highly charged cationic polymer Polyquaternium-37 dispersed in a carrier ester of propylene glycol dicaprylate dicaprylate and PPG-1 trideceth-6. Propylene glycol dicaprylate dicaprylate is a mixture of the propylene glycol diesters of caprylic and capric acids, also known by its technical name of Decanoic Acid, 1-Methyl-1,2-Ethanediyl Ester mixed with 1-Methyl-1,2-ethanediyl dioctanoate. Trideceth-6 is the polyethylene glycol ether of tridecyl alcohol that conforms generally to the formula: $C_{13}H_{27}(OCH_2CH_2)_nOH$ where n has an average value of 6.

The polymeric quaternary ammonium salt is employed in compositions in amounts sufficient to reducing the rupture of nematocysts from jellyfish. Such amounts can range from about 0.25% to about 20% or more, preferably from about 0.5–1 to about 5%, most preferably from about 2% to about 5%. Such polymeric quaternary ammonium salts have the advantage of being used as an emulsifier to improve the form or viscosity of the composition.

Other emulsifiers can include, for example, Promulgen G non-ionic emulsifier, trade name of the Amerchol Corporation. Brij 52 (Ceteth-2) and Brig 56 (Ceteth-10) are trade names of ICI Americas, Wilmington Del. 19897.

Conveniently, the quantity of water-in-oil emulsifier found useful in the compositions of the present invention is the range of about 0.5 to about 5 weight percent of composition.

Sunscreen Actives

The present composition and/or method can be employed in skin protectants and sunscreens which also offer protection against solar radiation and other environmental insults. The present composition can also be employed in a cosmetic moisturizer which could be utilized by a consumer near the water when the possibility exists for jellyfish contact.

Accordingly, the compositions of the present invention can contain a sunscreening effective amount of one or more oil-soluble sunscreening UV-B actives or a mixture of one or more UV-B actives and one or more UV-A actives. UV-A type sunscreening actives protect against long wavelength actinic radiation of the sun in the 320 to 400 nm range and UV-B type sunscreening actives protect against shorter wavelength, actinic radiation of the sun in the 290–320 nm range.

Typical sunscreen actives include trade name of para-aminobenzoic acid up to about 15 weight percent or from about 5 to 15% in admixture with other sunscreen actives; cinoxate up to about 3 weight percent or about 1 to 3% in admixture; diethanolamine methoxycinnamate up to 10 weight percent or about 8 to 10% in admixture; digalloyl trioleate up to 5 weight percent or about 2 to 5% in admixture; dioxybenzone up to 3 weight percent alone or in admixture; ethyl 4-[bis(hydroxypropyl)]aminobenzoate up to 5 weight percent or about 1 to 5% in admixture; glyceryl aminobenzoate up to 3 weight percent or about 2 to 3% in admixture; homosalate up to 15 weight percent or about 4 to 15% in admixture; lawsone up to 0.25 weight percent with dihydroxyacetone up to 3 weight percent; menthyl anthranilate up to 5 weight percent or about 3 to 5% in admixture; octocrylene up to 10 weight percent or 7 to about 10% in admixture; octyl methoxycinnamate up to 7.5 weight percent or about 2 to 7.5% in admixture; octyl salicylate up to 5 weight percent or about 3 to 5% in admixture; oxybenzone up to 6 weight percent or about 2 to 6% in admixture; padimate up to 8 weight percent or about 1.4 to 8% in admixture; phenylbenzimidazole sulfonic acid up to 4 weight percent or about 1 to about 4% in admixture; red veterinary petrolatum up to 95 percent or about 30 to 95% in admixture; sulisobenzone up to 10 weight percent or about 5 to 10% in admixture; titanium dioxide up to 25 weight percent or about 2 to 25% in admixture; and trolamine salicylate up to 12 weight percent or about 5 to 12% in admixture.

Typical suitable UV-B type sunscreening actives include octyl para-methoxycinnamate available from Givaudan Corporation, Clifton, N.J., under the trade name of Parsol MCX and Parsol 1789, usually present in the range of about 1.5 to about 7.5 weight %, or octyl salicylate available from Harmann and Riemer, Springfield, N.J., 07081, usually in the range of about 3 to about 5 weight %, of the total sunscreen composition or emulsion. The amount of UV-B type sunscreening active should be sufficient to give an SPF of at least 2 to 15.

A typical suitable UV-A type sunscreening actives include benzophenone-3, usually in the range of about 0.5 to about 6 weight %. Such active can be obtained from Rhone-Poulenc, Atlanta, Ga.

Sunscreen emulsions containing mixtures of UV-B and UV-A type sunscreen actives should be sufficient to provide an SPF of 4 to 50.

water

Water may be used as a diluent or can be the internal (discontinuous) or external (discontinuous) phase of an emulsion system.

emollients

An emollient is an oil-containing agent which helps to smooth and soften the skin, and may also reduce its roughness, cracking or irritation. Typical suitable cosmetic emollients include mineral, oil, having a viscosity in the range of 50 to 500 SUS, lanolin oil, coconut oil, cocoa butter, olive oil, almond oil, macadamia nut oil, aloe extract, jojoba oil, safflower oil, corn oil, liquid lanolin, cottonseed oil and peanut oil.

Other typical suitable cosmetic emollients include Purcellin oil, perhydrosqualene, castor oil, polybutene, odorless mineral spirits, sweet almond oil, avocado oil, calophyllum oil, ricin oil, vitamin E acetate, olive oil, silicone oils such as dimethylopolysiloxane and cyclomethicone, linolenic alcohol, oleyl alcohol, the oil of cereal germs such as the oil of wheat germ, isopropyl palmitate, isopropyl myristate, hexadecyl stearate, butyl stearate, decyl oleate, acetyl glycerides, the octanoates and benzoates of ($C_{12}$–$C_{15}$) alcohols, the octanoates and decanoates of alcohols and polyalcohols such as those of glycol and glycerol, ricin oleates of alcohols and poly alcohols such as those of isopropyl adipate, hexyl laurate and octyl dodecanoate.

Other typical suitable cosmetic emollients which are solids or semi-solids at ambient temperatures may be use if admixed with mineral oil or mineral oil extra heavy in amounts sufficient to provide liquid topical compositions. Such solid or semi-solid cosmetic emollients include hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate.

Typical suitable emollients include esters of a straight or branched-chain $C_{10}$–$C_{16}$ alcohol and a straight or branched chain C4–C20 mono- and dicarboxylic acids include the straight and branched chain monocarboxylic acids substituted by hydroxy or double bonds including monocarboxylic acids such as: butanoic, pentanoic, 2-methyl- and 3-methyl-pentanoic, 2,2-dimethylpropanoic, hexanoic, 2-methyl-, 3-methyl-, and 4-methyl-, 5-methyl- and 6-methyl-heptanoic, 2-ethylhexanoic, octanoic (caprylic), 2-methyl-, 3-methyl-, 4-methyl-, 5-methyl-, 6-methyl-, 7-methyl- and 8-methyl-nonanoic, 3,3,5-trimethylexanoic (isonanomic), decanoic (caproic), 2-methyl-, 3-methyl-, 4-methyl-, 5-methyl-, 6-methyl-, 7-methyl-, 8-methyl-, 9-methyldecanoic, undecanoic, dodecanoic (lauric), dineopentylacetic, methyl-t-butyineopentylacetic, tridecanoic, tetradecanoic (myristic), pentadecanoic, hexadecanoic (palmitic), heptadecanoic (margaric), octadecanoic (stearic), hydroxystearic 16-methylheptadecanoic (isistearic), double bond subsituted (unsaturated) carboxylic acids such as oleic(cis-9-octadecenoic), linoleic(cis, cis-9, 12-octadecadienoic) and linolenic cis,cis,cis-9,12,15-octadecadienoic acid), nonadecanioc and $CH_3(CH_2)_{18}CO_2H$.

Typical suitable $C_4$–$C_{20}$ dicarboxylic acids include dicarboxylic acids of the formula $(CH_2)_n (CO_2H)_2$ wherein n is 2 to 18 including succinic (n=2), glutaric (n=3), adipic (n=4), pimelic (n=5), suberic (n=6), azelaic (n=7), sebacic (n=8) as well as the $C_{12}$, $C_{16}$ and $C_{19}$ members such as Brassilic ($C_{13}$), thapsic ($C_{16}$) and nonadecane-1,19- dicarboxylic acid. The preferred dicarboxylic acids are succinic and adipic.

Typically suitable tri (lower alkyl) substituted benzoic acid include trimethylbenzoic acids, such as 1,1,3-trimthylbenzoic acid, 1,2,4-trimethyl-benzoic acid (trimellitic acid), and 1,3,5-trimethylbenzoic acid (trimesic acid). The preferred tri (loweralkyl) benzoic acid is trimellitic acid.

Preferred esters of $C_4$ to $C_{20}$ monocarboxylic acids and straight and branched chain C10–C16 alcohols include tridecyl neopentonate, isotridecyl isononanoate, isodecyl neopentonate, isodecyl hydroxystearate, isodecyl laurate, isodecyl myristate, isodecyl oleate, isodecyl palmitate, decyl oleate, and isocetyl palmitate (isohexadecyl hexadecanoate) and iso-hexadecyl isodecanoate (14-methylpentadecyl-8-methyinonanoate).

The preferred esters of straight and branched-chain C10–C16 alcohols and C4–C20 dicarboxylic acids is decyl succinate. The preferred esters of straight and branched-chain C10–C16 esters of tri(loweralkyl) substituted benzoic acids are the decyl, isodecyl, isotridecyl and tridecyl esters of trimethylbenzoic acids especially trimellitic acid; tridecyl trimellitate is more preferred.

The emollient can be a mixture of tridecyl trimellitate and tridecyl stearate or a mixture of tridecyl trimellitate, tridecyl stearate, neopentyl glycol dicaprylate and neopentyl dicaprate such as is available from Lipo Chemicals Inc., Patterson, N.J. under the trade name Lipovol MOS-70. The emollient component can optionally be included in the sunscreen composition in an amount ranging from about 10 to about 50 weight percent, preferably about 20 to about 40 percent.

dry-feel modifier

A dry-feel modifier is an agent which gives a sunscreen a "dry feel" upon drying, and may reduce sunscreen migration and can include silazane treated silica, precipitated silica, fumed silica or mixtures thereof. The dry-feel modifier can optionally be included in the sunscreen composition in amounts ranging from about 0.1 to about five weight percent, preferably from about 0.3 to about 1.5%.

waterproofing agents

A waterproofing agent is a material added to the composition to assist in retaining the sunscreen active on the skin. Typical suitable waterproofing agents for sunscreen raw materials include copolymers derived from polymerization of octadecene-1 and maleic anhydride in accordance with the published procedures such as those in U.S. Pat. No. 3,860,700 and Reissue No. 28,475. The preferred waterproofing agent is a copolymer commercially available from Chevron Chemicals Co. under the trade name, PA-18 polyanhydride resin.

By the term "waterproofing effective amount of at least one waterproofing agent" means the waterproofing agent(s) is applied in amounts effective to allow the sunscreen to remain on the skin after exposure to circulating water for at least 80 minutes using the procedures described in "Sunscreen Drug Products for OTC Human Use", Federal Register, Vol. 43, Aug. 25, 1978, Part 2, pages 38206–38269. The waterproofing agent can optionally be included in the sunscreen composition in an amount ranging from about 0.01 to about 10.0 weight percent, preferably about 1.0 to about 10.0 percent.

antimicrobial preservative

An antimicrobial preservative is a substance or preparation which destroys, prevents or inhibits the multiplication/growth of microorganisms in the sunscreen composition and may offer protection from oxidation. Preservatives are used to make aqueous products self-sterilizing. This is done to prevent the development of microorganisms that may be in the product from growing during manufacturing and distribution of the product and during use by consumers who may inadvertently contaminate the products during normal use. Typical preservatives include the lower alkyl esters of para-hydroxybenzoates (parabens) especially, methyl paraben, isobutyl paraben and mixtures thereof, and benzoic acid. The antimicrobial preservative can optionally be included in the sunscreen composition in an amount ranging from about 0.05 to about one percent, preferably about 0.2 to about 0.5 percent. One exemplary preservative is Germaben II, trade name of Sutton Labs, Chatham, N.J.

antioxidants

An antioxidant is a natural or synthetic substance added to the sunscreen to protect from or delay its deterioration due to the action of oxygen in the air (oxidation). Anti-oxidants prevent oxidative deterioration which may lead to the generation of rancidity and nonenyzymatic browning reaction products. Typical suitable antioxidants include propyl, octyl and dodecyl esters of gallic acid, butylated hydroxyanisole (BHA)(usually as a mixture of orthos and meta isomers), butylated hydroxytoluene (BHT) and nordihydroguaiaretic acid. The antioxidant can optionally be included in the sunscreen composition in an amount ranging from about 0.02 to about one weight percent, preferably about 0.05 to about 0.1 percent.

toxin neutralizing agents

The composition may optionally, also contain substance capable of neutralizing toxins from jellyfish. Such substances can include protease enzymes such as papain or trypsin; lipase enzymes including phospholipases; acids such as dilute acetic acid (vinegar) or bases such as baking soda which can lower or raise the pH of the composition; salts which can raise its ionic strength; chelators such as EDTA; or sulfhydryl bonding or breaking agents such as thioglycolate.

antifoaming agents

Antifoaming agents, also known as defoaming agents, are substance used to reduce foaming due to proteins, gases or nitrogenous materials which may interfere during processing. Examples include 2-octanol, sulfonated oils, organic phosphates, silicone fluids, dimethylpolysiloxane, etc. One defoaming agent is DC200 fluid, trade name of the Dow Corning Corporation, Midland, Mich.

fragrances

Fragrances are aromatic compounds which can impart an aesthetically pleasing aroma to the sunscreen composition. Typical fragrances include aromatic materials extracted from botanical sources (i.e. rose petals, gardenia blossoms, jasmine flowers, etc.) which can be used alone or in any combination to create essential oils. Alternatively, alcoholic extracts may be prepared for compounding fragrances. The fragrance can optionally be included in the sunscreen composition in an amount ranging from about 0.01 to about five weight percent, preferably about 0.1 to about two percent.

Definitions and suppliers of the ingredients used in the following illustrative examples may be found in the CTFA Cosmetic Ingredient Dictionary, published by the Cosmetic, Toiletry and Fragrance Association, Inc., 1110 Vermont Avenue, NW, Wash. D.C. 20005, Third Edition 1982. All proportions are by percent weight.

The following examples serve to illustrate the present invention but as such, should not be construed as limiting the overall scope of the same.

EXAMPLE 1

Effect of Compositions on Nematocyst Rupture

An oil-in-water emulsion or lotion composition is prepared using the following ingredients.

| Ingredient | Weight % |
| --- | --- |
| Salcare SC96 (contains Polyquaternium-37) | 2 |
| Mineral Oil | 5 |
| Water | 93 |
| Total | 100% |

The composition is prepared by mixing Salcare SC96 with mineral oil until uniform and rapidly mixing the resultant mixture with water until a uniform emulsion results.

Tests are conducted with various topical compositions on gelatin coated glass slides where the gelatin are prepared using ambient salt water. Compositions are applied at 2 microliters per square centimeter ($\mu l/cm^2$). Adult sea nettles and Portuguese man-of-war provide the nematocysts. Jellyfish tentacles are placed upon or dragged across the treated slides for 10 to 15 seconds to allow the jellyfish to fire its nematocysts. The nematocysts are examined microscopically to count those nematocysts which ruptured and those which did not. Controls are performed by placing the tentacles directly on the gelatin slides. The results indicate that the composition of Example 1 effectively reduces nematocyst rupture of the sea nettles to less than 3% and the Portuguese man-of-war to less than 10%. In contrast, the gelatin coated glass slides and gelatin coated glass slides coated with mineral oil are not effective, as indicated by the 96.1 and 100% nematocyst rupture, respectively.

EXAMPLES 2 AND 3

Oil-in-water emulsions are prepared using the following ingredients.

| Ingredient | Weight % | |
| --- | --- | --- |
| Merquat 550 (contains Polyquaternium-7) | 12.5 (equivalent to 1% solids) | — |
| Polymer JR-30M (contains Polyquaternium-10) | — | 1.0 |
| Cetyl alcohol | 0.3 | 0.3 |
| DC 200 fluid (antifoaming agent) | 0.3 | 0.3 |
| Mineral oil extra heavy | 2.0 | 2.0 |
| Promulgen G (emulsifier) | 6.5 | 6.5 |
| Germaben II (preservative) | 1.0 | 1.0 |
| Brij 52 (emulsifier) | 0.82 | 0.82 |
| Brij 56 (emulsifier) | 1.18 | 1.18 |
| Water | 75.4 | 86.9 |
| Total | 100 | 100 |

The water is heated to 71–77° C. The Brij 56 is added, mixed until uniform and either the Merquat 550 or Polymer JR-30M is added and mixed to give a uniform aqueous phase. The Promulgen G, mineral oil extra heavy, Brij 52, cetyl alcohol and DC 200 fluid are combined, heated to 71–77° C. and stirred until all are dissolved to give a uniform oil phase. With rapid mixing, the oil phase is added to the aqueous phase mixed for at least 5 minutes, forced cooled to 49–54° C. and slowly mixed. The Germaben II is added and mixed well to give an oil-in-water emulsion.

The same test procedures are employed as in Example 1, except that different emulsions are employed and only the adult sea nettle provides the nematocysts. The results indicate that each emulsion containing a polymeric quaternary ammonium salt effectively reduces rupture of small nematocysts compared with a control which lacks a polymeric quaternary ammonium salt.

We claim:

1. A method for protecting the skin from jellyfish stings, comprising topically contacting the skin with a composition containing a polymeric quaternary ammonium salt in amounts sufficient to protect against the rupture of jellyfish nematocysts.

2. The method of claim 1 wherein said polymeric quaternary ammonium salt is Polyquaternium-7, Polyquaternium-10, Polyquaternium-37 or mixtures thereof.

3. The method of claim 1 wherein said polymeric quaternary ammonium salt is Polyquaternium-37.

4. The method of claim 1 wherein said composition is in the form of an emulsion, liquid dispersion, solution, skin cream, face cream, lotion or ointment.

5. The method of claim 1 wherein said composition is in the form of an emulsion.

6. The method of claim 1 wherein said composition is in the form of a oil-in-water emulsion.

7. The method of claim 1 wherein said composition is in the form of an emulsion, liquid dispersion, solution, skin cream, face cream, lotion or ointment containing a sunscreen active to protect against the actinic radiation of the sun.

8. The method of claim 1 wherein said amount of polymeric quaternary ammonium salt in the composition ranges from about 0.25% to about 20 weight %.

9. The method of claim 1 wherein said amount of polymeric quaternary ammonium salt in the composition ranges from about 0.5% to about 5 weight %.

10. An article of manufacture comprising packaging material and a composition comprising a protective agent which is a polymeric quaternary ammonium salt contained within said packaging material, wherein said protective agent is effective in protecting against the rupture or stings of jellyfish nematocysts and wherein said packaging material comprises a label which indicates that said protective agent can be used to protect against jellyfish stings.

11. The article of manufacture of claim 10 wherein said polymeric quaternary ammonium salt is Polyquaternium-7, Polyquaternium-10, Polyquaternium-37 or mixtures thereof.

12. The article of manufacture of claim 10 wherein said polymeric quaternary ammonium salt is Polyquaternium-37.

13. The article of manufacture of claim 10 wherein said composition is in the form of an emulsion, liquid dispersion, solution, skin cream, face cream, lotion or ointment.

14. The article of manufacture of claim 10 wherein said composition is in the form of an emulsion.

15. The article of manufacture of claim 10 wherein said composition is in the form of a oil-in-water emulsion.

16. The article of manufacture of claim 10 wherein said composition is in the form of an emulsion, liquid dispersion, solution, skin cream, face cream, lotion or ointment containing a sunscreen active to protect against the actinic radiation of the sun.

17. The article of manufacture of claim 10 wherein said composition is in the form of an oil-in-water emulsion containing a sunscreen active to protect against the actinic radiation of the sun.

18. The article of manufacture of claim 10 wherein the amount of polymeric quaternary ammonium salt in the composition ranges from about 0.25% to about 20 weight %.

19. The article of manufacture of claim 10 wherein the amount of polymeric quaternary ammonium salt in the composition ranges from about 0.5% to about 5 weight %.

* * * * *